United States Patent [19]
Gershony et al.

[11] Patent Number: 5,868,778
[45] Date of Patent: Feb. 9, 1999

[54] VASCULAR SEALING APPARATUS AND METHOD

[75] Inventors: Gary Gershony, El Macero, Calif.;
Daniel J. Kasprzyk, Fogelsville, Pa.;
Michael J. Horzewski, San Jose, Calif.

[73] Assignee: Vascular Solutions, Inc., Minneapolis, Minn.

[21] Appl. No.: 850,477

[22] Filed: May 5, 1997

Related U.S. Application Data

[63] Continuation of Ser. No. 549,332, Oct. 27, 1995, Pat. No. 5,626,601.

[51] Int. Cl.$^6$ .................................................... A61M 29/00
[52] U.S. Cl. ............................. 606/194; 604/101; 604/96
[58] Field of Search .................................... 606/194, 108, 606/192, 191, 213; 604/96, 101

[56] References Cited

U.S. PATENT DOCUMENTS

| | | |
|---|---|---|
| Re. 34,866 | 2/1995 | Kensey et al. . |
| 802,190 | 10/1905 | Heineman . |
| 1,191,736 | 7/1916 | Roberson . |
| 1,794,221 | 2/1931 | Washburn et al. . |
| 2,169,947 | 8/1939 | Freudenberg . |
| 2,492,458 | 12/1949 | Bering, Jr. . |
| 2,533,004 | 12/1950 | Ferry et al. . |
| 2,814,294 | 11/1957 | Figge . |
| 2,898,913 | 8/1959 | Ritter et al. . |
| 3,016,895 | 1/1962 | Sein . |
| 3,056,408 | 10/1962 | Brown . |
| 3,447,533 | 6/1969 | Spicer . |
| 3,516,403 | 6/1970 | Cournut . |
| 3,540,431 | 11/1970 | Mobin-Uddin . |
| 3,572,335 | 3/1971 | Robinson . |
| 3,675,639 | 7/1972 | Cimber . |
| 3,728,207 | 4/1973 | Heling . |
| 3,766,924 | 10/1973 | Pidgeon . |
| 3,800,792 | 4/1974 | McKnight et al. . |

(List continued on next page.)

FOREIGN PATENT DOCUMENTS

| | | |
|---|---|---|
| 0476178A1 | 3/1992 | European Pat. Off. . |
| 0482350A2 | 4/1992 | European Pat. Off. . |
| 0493810A1 | 7/1992 | European Pat. Off. . |
| 2641692 | 7/1990 | France . |

(List continued on next page.)

OTHER PUBLICATIONS

Bierman, et al., "Portal Venipuncture. A Percutaneous, Trans–Hepatic Approach," *Proceedings of the Society for Experimental Biology and Medicine*, vol. 79, No. 3, pp. 550–552, Mar. 1952.

Berkowitz, et al., "New Technique for Control of Ruptured Abdominal Aortic Aneurysm," *Surgery, Gynecology & Obstetrics*, pp. 107–109, Jul. 1971.

Arbulu, et al., "Control of Bleeding from a Gunshot Wound of the Inferior Vena Cava at its Junction with the Right Atrium by Means of a Foley Catheter," *The Journal of Thoracic and Cardiovascular Surgery*, vol. 63, No. 3, pp. 427–429, Mar. 1972.

(List continued on next page.)

*Primary Examiner*—Michael Buiz
*Assistant Examiner*—Kevin Truong
*Attorney, Agent, or Firm*—Patterson & Keough, P.A.

[57] ABSTRACT

A vascular sealing device for effecting closure of a puncture or other opening in a blood vessel, or other body cavity, which has been entered through percutaneous techniques. The device is useable with a standard percutaneous vascular introducer. The vascular sealing device generally comprises a body or shaft, an adapter disposed at a proximal end of the shaft, and a balloon portion disposed generally at a distal end of the shaft. A core wire is connected to the distal end and extends, internally, through a lumen of the device for deflation of the balloon. A procoagulant is introduced through the introducer, or alternatively through an additional lumen and associated apertures, and to the puncture sealed by the inflated balloon. Subsequently, the balloon is deflated and the device is removed from the sealing puncture, with or without the aid of a reaccess sheath.

41 Claims, 6 Drawing Sheets

U.S. PATENT DOCUMENTS

| | | |
|---|---|---|
| 3,903,882 | 9/1975 | Augurt . |
| 3,972,328 | 8/1976 | Chen . |
| 3,996,938 | 12/1976 | Clark, III . |
| 4,016,877 | 4/1977 | Cruz, Jr. et al. . |
| 4,060,081 | 11/1977 | Yannas et al. . |
| 4,066,083 | 1/1978 | Ries . |
| 4,080,970 | 3/1978 | Miller . |
| 4,148,664 | 4/1979 | Cruz, Jr. et al. . |
| 4,167,945 | 9/1979 | Gottlieb . |
| 4,215,686 | 8/1980 | Gregory et al. . |
| 4,238,480 | 12/1980 | Sawyer . |
| 4,327,722 | 5/1982 | Groshong et al. . |
| 4,341,207 | 7/1982 | Steer et al. . |
| 4,347,841 | 9/1982 | Benyó et al. . |
| 4,364,392 | 12/1982 | Strother et al. . |
| 4,390,519 | 6/1983 | Sawyer . |
| 4,393,080 | 7/1983 | Pawelchak et al. . |
| 4,404,970 | 9/1983 | Sawyer . |
| 4,407,787 | 10/1983 | Stemberger . |
| 4,516,968 | 5/1985 | Marshall et al. . |
| 4,570,629 | 2/1986 | Widra . |
| 4,572,186 | 2/1986 | Gould et al. . |
| 4,576,817 | 3/1986 | Montgomery et al. . |
| 4,578,067 | 3/1986 | Cruz, Jr. . |
| 4,606,910 | 8/1986 | Sawyer . |
| 4,614,794 | 9/1986 | Easton et al. . |
| 4,650,466 | 3/1987 | Luther . |
| 4,655,210 | 4/1987 | Edenbaum et al. . |
| 4,655,211 | 4/1987 | Sakamoto et al. . |
| 4,669,474 | 6/1987 | Barrows . |
| 4,676,782 | 6/1987 | Yamamoto et al. . |
| 4,725,671 | 2/1988 | Chu et al. . |
| 4,738,255 | 4/1988 | Goble et al. . |
| 4,774,091 | 9/1988 | Yamahira et al. . |
| 4,775,585 | 10/1988 | Hagiwara et al. . |
| 4,784,653 | 11/1988 | Bolton et al. . |
| 4,789,401 | 12/1988 | Ebinger et al. . |
| 4,793,351 | 12/1988 | Landman et al. . |
| 4,841,962 | 6/1989 | Berg et al. . |
| 4,847,049 | 7/1989 | Yamamoto . |
| 4,856,504 | 8/1989 | Yamamoto et al. . |
| 4,867,748 | 9/1989 | Samuelsen . |
| 4,891,359 | 1/1990 | Saferstein et al. ............................ 37/12 |
| 4,892,519 | 1/1990 | Songer et al. . |
| 4,897,081 | 1/1990 | Poirier et al. . |
| 4,911,898 | 3/1990 | Hagiwara et al. . |
| 4,915,694 | 4/1990 | Yamamoto et al. . |
| 4,925,924 | 5/1990 | Silver et al. . |
| 4,994,033 | 2/1991 | Shockey et al. . |
| 5,041,093 | 8/1991 | Chu . |
| 5,049,132 | 9/1991 | Shaffer et al. . |
| 5,060,642 | 10/1991 | Gilman . |
| 5,085,646 | 2/1992 | Svenson et al. . |
| 5,098,397 | 3/1992 | Svensson et al. . |
| 5,123,914 | 6/1992 | Cope . |
| 5,156,592 | 10/1992 | Martin et al. . |
| 5,156,595 | 10/1992 | Adams . |
| 5,192,300 | 3/1993 | Fowler . |
| 5,192,302 | 3/1993 | Kensey et al. . |
| 5,207,651 | 5/1993 | Snyder . |
| 5,213,567 | 5/1993 | Masaki . |
| 5,221,259 | 6/1993 | Weldon et al. . |
| 5,236,421 | 8/1993 | Becher . |
| 5,242,415 | 9/1993 | Kantrowitz et al. . |
| 5,246,421 | 9/1993 | Saab . |
| 5,264,218 | 11/1993 | Rogozinski . |
| 5,275,616 | 1/1994 | Fowler . |
| 5,282,827 | 2/1994 | Kensey et al. . |
| 5,290,310 | 3/1994 | Makower et al. . |
| 5,292,332 | 3/1994 | Lee . |
| 5,308,313 | 5/1994 | Karami et al. . |
| 5,312,435 | 5/1994 | Nash et al. . |
| 5,324,306 | 6/1994 | Makower et al. . |
| 5,328,471 | 7/1994 | Slepian . |
| 5,336,178 | 8/1994 | Kaplan et al. . |
| 5,364,357 | 11/1994 | Aase . |
| 5,364,367 | 11/1994 | Banks et al. . |
| 5,383,896 | 1/1995 | Gershony . |
| 5,391,183 | 2/1995 | Janzen et al. . |
| 5,411,520 | 5/1995 | Nash et al. . |
| 5,413,571 | 5/1995 | Katsaros et al. . |
| 5,419,765 | 5/1995 | Weldon et al. . |
| 5,431,639 | 7/1995 | Shaw . |
| 5,437,631 | 8/1995 | Janzen . |
| 5,441,517 | 8/1995 | Kensey et al. . |
| 5,443,481 | 8/1995 | Lee . |
| 5,454,833 | 10/1995 | Boussignac et al. . |
| 5,759,173 | 6/1998 | Preissman et al. ........................ 604/96 |
| 5,776,100 | 7/1998 | Forman ................................... 606/194 |

FOREIGN PATENT DOCUMENTS

| | | |
|---|---|---|
| 8907370 | 9/1989 | Germany . |
| 1509023 | 4/1978 | United Kingdom . |
| 1569660 | 6/1980 | United Kingdom . |
| 2057269 | 4/1981 | United Kingdom . |
| WO89/11301 | 11/1989 | WIPO . |
| WO90/14796 | 12/1990 | WIPO . |
| WO91/09641 | 7/1991 | WIPO . |
| WO92/22252 | 12/1992 | WIPO . |
| WO93/07928 | 4/1993 | WIPO . |

OTHER PUBLICATIONS

Okuda, et al., "Percutaneous Transhepatic Catheterization of the Portal Vein for the Study of Portal Hemodynamics and Shunts," *Gastroenterology*, vol. 73, No. 2, pp. 279–284, Aug. 1977.

Viamonte, Jr. et al., "Selective Catheterization of the Portal Vein and its Tributaries," *Radiology*, vol. 114, pp. 457–460, Feb. 1975.

Takayasu, et al., "Intrahepatic Portal Vein Branches Studied by Percutaneous Transhepatic Portography," *Radiology*, vol. 154, No. 1, pp. 31–36, Jan. 1985.

Lunderquist, et al., "Transhepatic Catheterization and Obliteration of the Coronary Vein in Patients with Portal Hypertension and Esophageal Varices," *The New England Journal of Medicine*, vol. 291, No. 13, pp. 646–649, Sep. 26, 1974.

Scott, et al., "Percutaneous Transhepatic Obliteration of Gastro–Esophageal Varices," *The Lancet*, pp. 53–55, Jul. 10, 1976.

Thomas, "Control of Bleeding in Complicated Peripheral Vascular Lesions," *Surgery, Gynecology & Obstetrics*, pp. 1015–1018, Jun. 1971.

Takayasu, et al, "A New Hemostatic Procedure for Percutaneous Transhepatic Portal Vein Catheterization," *Japanese Journal of Clinical Oncology*, vol. 18, No. 3, pp. 227–230, 1988.

Gupta, et al., "The Role of Intra–aortic Balloon Occlusion in Penetrating Abdominal Trauma," *The Journal of Trauma*, vol. 29, No. 6, pp. 861–865, Jun. 1989.

McAnena, et al., "Insertion of a Retrohepatic Vena Cava Balloon Shunt Through the Saphenofemoral Junction," *The American Journal of Surgery*, vol. 158, No. 5, pp. 463–466, Nov. 1989.

Tobin, et al., "Plugged Liver Biopsy in Patients with Impaired Coagulation," *Digestive Diseases and Sciences*, vol. 34, No. 1, pp. 13–15, Jan. 1989.

Pfab, et al., "Local Hemostasis of Nephrostomy Tract with Fibrin Adhesive Sealing in Percutaneous Nephrolithotomy," *European Urology*, vol. 13, pp. 118–121, 1987.

Burrows, et al., "A 4–F Coaxial Catheter System for Pediatric Vascular Occlusion with Detachable Balloons," *Radiology*, vol. 170, No. 3, part. 2, pp. 1091–1094, Mar. 1989.

Sclafani, et al., "Transcatheter Treatment of Injuries to the Profunda Femoris Artery," *American Journal of Roentgenology*, vol. 138, pp. 463–466, Mar. 1982.

Abbott, et al, "Microcrystalline Collagen as a Topical Hemostatic Agent for Vascular Surgery," *Surgery*, vol. 75, No. 6, pp. 926–933, Jun. 1974.

Silverstein, et al., "Experimental and Clinical Experiences with Collagen Fleece as a Hemostatic Agent," *The Journal of Trauma*, vol. 21, No. 5, pp. 388–393. May 1981.

Chvapil, et al., "Experimental Experiences with the Collagen Sponge as Hemostaticum and Tampon," *Journal of Biomedical Material and Research*, vol. 2, pp. 245–264, 1968.

Allison, et al., "Percutaneous Liver Biopsy and Track Embolization with Steel Coils," *Radiology*, vol. 169, No. 1, pp. 261–263, Oct. 1988.

Chvapil, et al., "Medical and Surgical Applications of Collagen," pp. 1–61, undated.

Behl, et al., "Foley Catheter in Cardiac Surgery," *The Italian Journal of Surgical Sciences*, vol. 17, No. 4, pp. 363–365, 1987.

Katzen, et al., "Treatment of Carotid–Cavernous Fistulas with Detachable Balloon Catheter Occlusion," *Advances in Ophthalmic, Plastic, and Reconstructive Surgery*, vol. 7, pp. 157–165, 1987.

Gallo, et al., "A Safe Technique for Removal of Massive Left Atrial Thrombus," *The Annals of Thoracic Surgery*, vol. 31, No. 3, pp. 283–284, Mar. 1981.

Ong, "Removal of Blunt Oesophageal Foreign Bodies in Children Using a Foley Catheter," *Australian Paediatric Journal*, vol. 18, No. 1, pp. 60–62, Mar. 1982.

Yellin, et al., "Vascular Isolation in Treatment of Juxtahepatic Venous Injuries," *Archives of Surgery*, vol. 102, No. 6, pp. 566–573, Jun. 1971.

Rösch, et al., "Experimental Catheter Obstruction of the Gastric Coronary Vein, Possible Technique for Percutaneous Intravascular Tamponade of the Gastroesophageal Varices," *Investigative Radiology*, vol. 10, No. 3, pp. 206–211, May–Jun. 1975.

Doty, et al., "Control of Hepatic Venous Bleeding By Transvenous Balloon Catheter," *Surgery, Gynecology & Obstetrics*, pp. 449–452, Sep. 1970.

Ansari, et al., "Foley Catheter for Salpingography, Pneumonography, Tubal Insufflation, and Hydrotubation," *Obstetrics and Gynecology*, vol. 50, No. 1, pp. 108–112, Jul. 1977.

Gembarowicz, et al., "Management of Variceal Hemorrhage," *Archives of Surgery*, vol. 115, No. 10, pp. 1160–1164, Oct. 1980.

Johnson & Johnson, "Now You Can Finally Collar Catheter Infection," *Critical Care Nurse*, Feb. 1994.

Hoyman, et al., "Hydrocolloid Wafer Dressings and Arterial Catheter Access Sites," *Ostomy/Wound Management*, pp. 22–27, Spring 1989.

Bhatnagar, et al., "Composites of Collagen with Synthetic Polymers for Biomedical Applications," *Advanced Concepts*, pp. 179–184, undated.

Datascope Corporation, "Instructions for Use Needle Depth Indicator Kit," pp. 1–2, undated.

Slaughter, et al., "A Single Center Randomized Trial Assessing Use of a Vascular Hemostasis Device vs. Conventional Manual Compression Following PTCA: What Are the Potential Resource Savings?," *Catheterization and Cardiovascular Diagnosis*, vol. 34, No. 3, pp. 210–214, Mar. 1995.

Cox, et al., "'How I Do It' — Head and Neck and Plastic Surgery, A Targeted Problem and its Solution, A Hemostatic Device for Endoscopic Surgery," *Laryngoscope*, vol. 98, No. 5, p. 579, May 1988.

Debrun, et al., "Two Different Calibrated–Leak Balloons: Experimental Work and Application in Humans," *American Journal of Neuroradiology*, vol. 3, pp. 407–414, Jul.–Aug. 1982.

Ruff, et al., "Percutaneous Vascular Intervention after Surgical Shunting for Portal Hypertension," *Radiology*, vol. 164, No. 2, pp. 469–474, Aug. 1987.

Panés, et al., "Efficacy of Balloon Tamponade in Treatment of Bleeding Gastric and Esophageal Varices Results in 151 Consecutive Episodes," *Digestive Diseases and Sciences*, vol. 33, No. 4, pp. 454–459, Apr. 1988.

Nguyen, et al., "Treatment of Coronary Artery Stenosis and Coronary Arteriovenous Fistula by Interventional Cardiology Techniques," *Catheterization and Cardiovascular Diagnosis*, vol. 18, No. 4, pp. 240–243, Dec. 1989.

Ridout, III, et al., "Hepatoportal Arteriovenous Fistula Treated with Detachable Balloon Embolotherapy," *The American Journal of Gastroenterology*, vol. 84, No. 1, pp. 63–66, Jan. 1989.

Krause, et al., "Utility of a Percutaneous Collagen Hemostasis Device: To Plug or Not to Plug?," *Journal of the American College of Cardiology*, vol. 22, No. 5, pp. 1280–1282, Nov. 1, 1993.

Sanborn, et al., "A Multicenter Randomized Trial Comparing a Percutaneous Collagen Hemostasis Device with Conventional Manual Compression after Diagnostic Angiography and Angioplasty," *Journal of the American College of Cardiology*, vol. 22, No. 5, pp. 1273–1279, Nov. 1, 1993.

Silverstein, et al., "Collagen Fibers as a Fleece Hemostatic Agent," *The Journal of Trauma*, vol. 20, No. 8, pp. 688–694, Aug. 1980.

Draney, et al., "ME210 Coronary Artery Bypass Surgery: Minimally Invasive Techniques," pp. 1–34, Jun. 13, 1995.

Von Hoch, et al., "Efficacy and Safety of Collagen Implants for Haemostasis of the Vascular Access Site after Coronary Balloon Angioplasty and Coronary Stent Implantation," *European Heart Journal*, vol. 16, No. 5, pp. 640–646, May 1995.

Datascope Corporation, "Instructions For Use: Vasoseal® Vascular Hemostatis Device," pp. 1–14, undated.

Riley, et al., "Percutaneous Liver Biopsy with Plugging of Needle Track: A Safe Method for Use in Patients with Impaired Coagulation," *The Lancet*, No. 8400, p. 436, Aug. 25, 1984.

Gazelle, et al., "Hemostatic Protein Polymer Sheath: Improvement in Hemostatis at Percutaneous Biopsy in the Setting of Platelet Dysfunction," *Radiology*, vol. 187, No. 1, pp. 269–272, Apr. 1993.

Abbott, et al., "The Effectiveness and Mechanism of Collagen–Induced Topical Hemostasis," *Surgery*, vol. 78, No. 6, pp. 723–729, Dec. 1975.

Chuang, et al., "Sheath Needle for Liver Biopsy in High–Risk Patients," *Radiology*, vol. 166, No. 1, pp. 261–262, Jan. 1988.

Chvapil, et al., "A Standardized Animal Model for Evaluation of Hemostatic Effectiveness of Various Materials," *The Journal of Trauma*, vol. 23, No. 12, pp. 1042–1047, Dec. 1983.

Richardson, et al., "Peripheral Vascular Complications of Coronary Angioplasty," *The American Surgeon*, vol. 55, No. 11, pp. 675–680, Nov. 1989.

Gazelle, et al., "Hemostatic Protein–Polymer Sheath: New Method to Enhance Hemostasis at Percutaneous Biopsy," *Radiology*, vol. 175, No. 3, pp. 671–674, Jun. 1990.

Kussmaul, III, et al., "Rapid Arterial Hemostasis and Decreased Access Site Complications after Cardiac Catheterization and Angioplasty: Results of a Randomized Trial of a Novel Hemostatic Device," *Journal of the American College of Cardiology*, vol. 25, No. 7, pp. 1685–1692, Jun. 1995.

Camenzind, et al., "Collagen Application Versus Manual Compression: A Prospective Randomized Trial for Arterial Puncture Site Closure after Coronary Angioplasty," *Journal of the American College of Cardiology*, vol. 24, No. 3, pp. 655–662, Sep. 1994.

Howard R. Bierman, Howard L. Steinbach, Laurens P. White, and Keith H. Kelly. *Portal Venipuncture. A Percutaneous, Trans–Hepatic Approach*. [Date], p. 551.

Kunio Okude, M.D., Koji Hirotaka Musha, M.D., and Noboru Arimizu, M.D., *Liver Physiology and Disease: Percutaneous Transhepatic Catheterization of the Portal Vein for hte Study of Portal Hemodynamics and Shunts*. 73:279–284, 1977, p. 280.

J. Scott, R. Dick, R.G. Long, Sheila Sherlock. *Percutaneous Transhepatic Obliteration of Gastro–Esophageal Varices*. The Lancet, Saturday, Jul. 10, 1976, pp. 54–55.

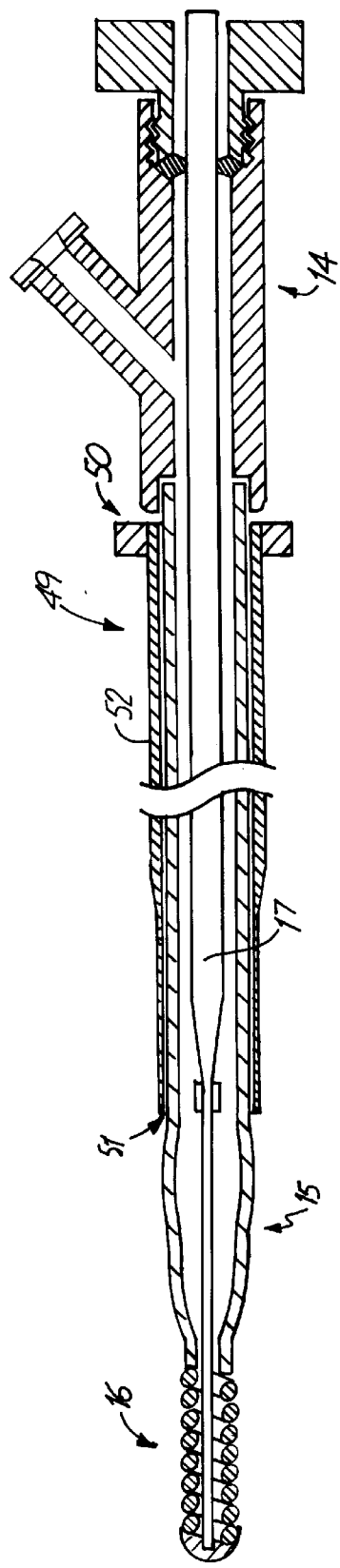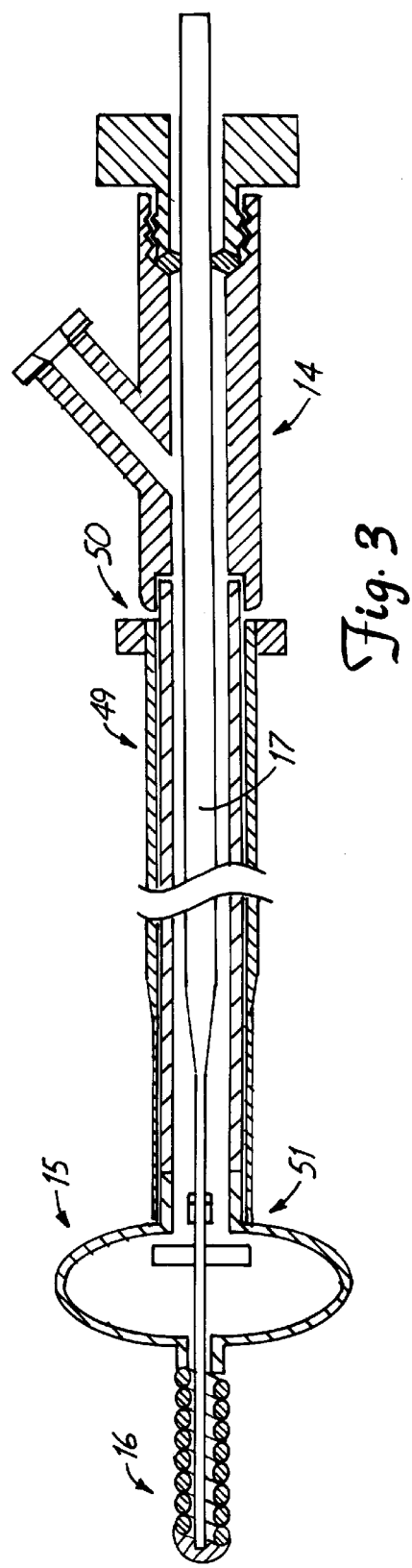

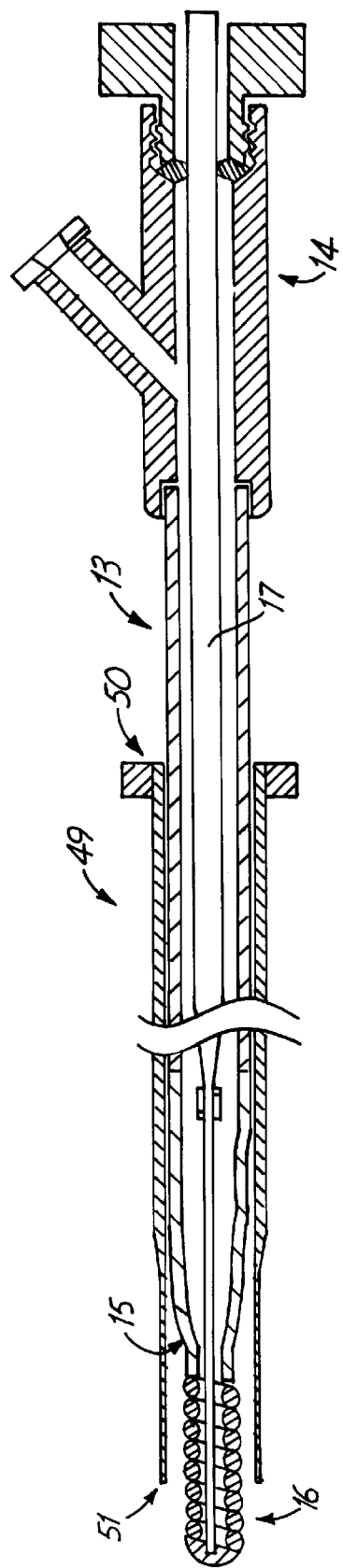

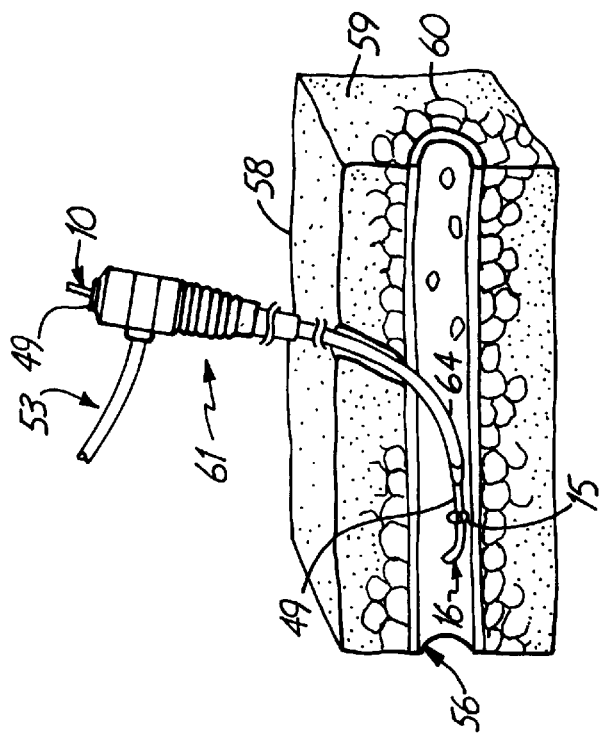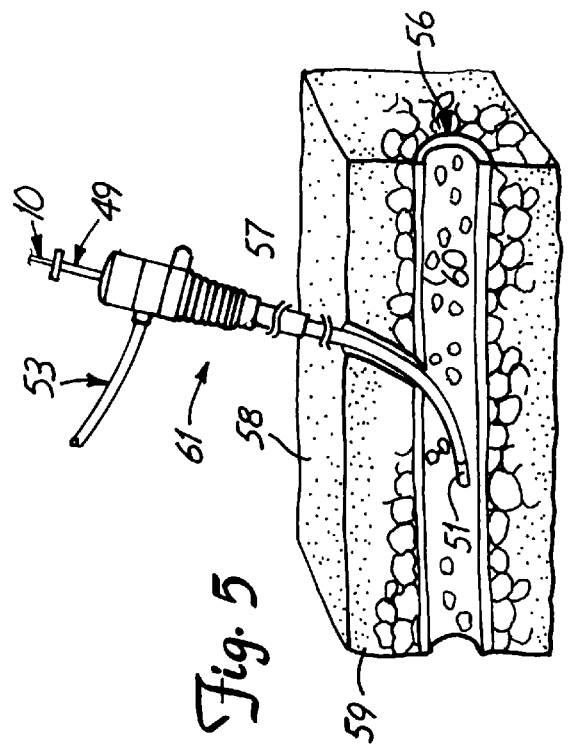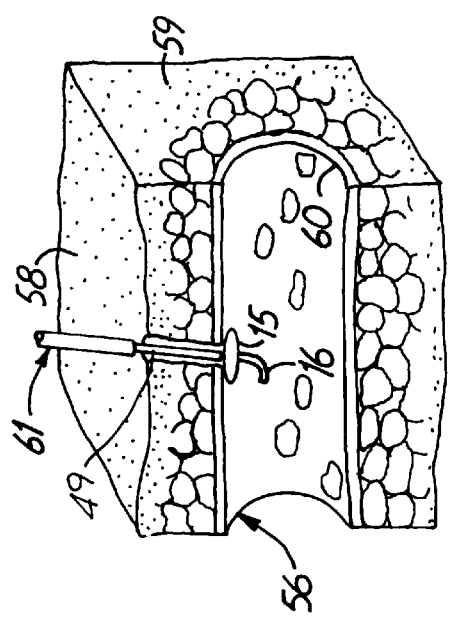

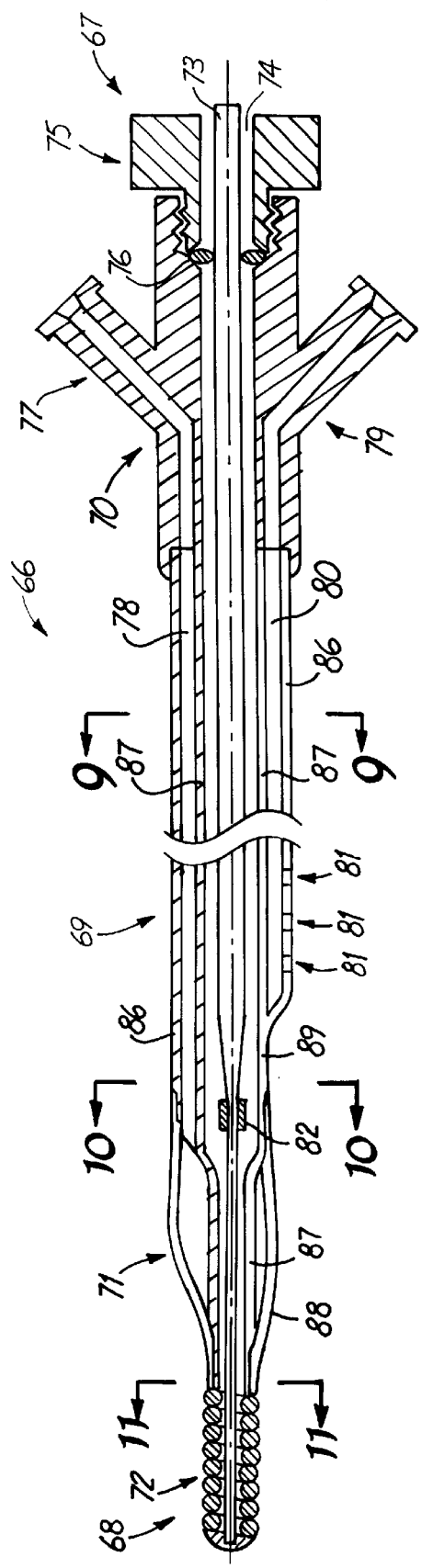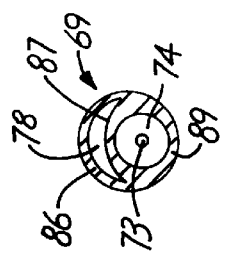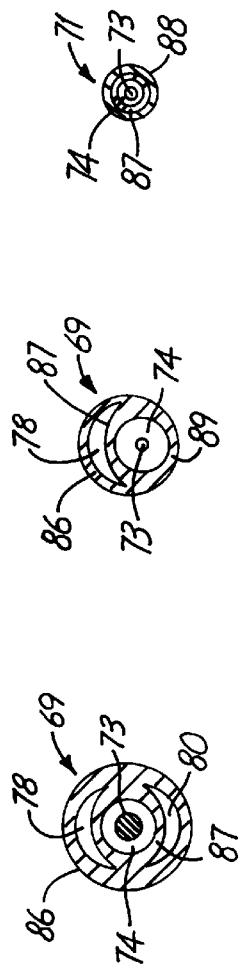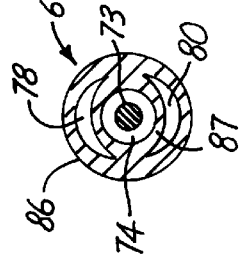

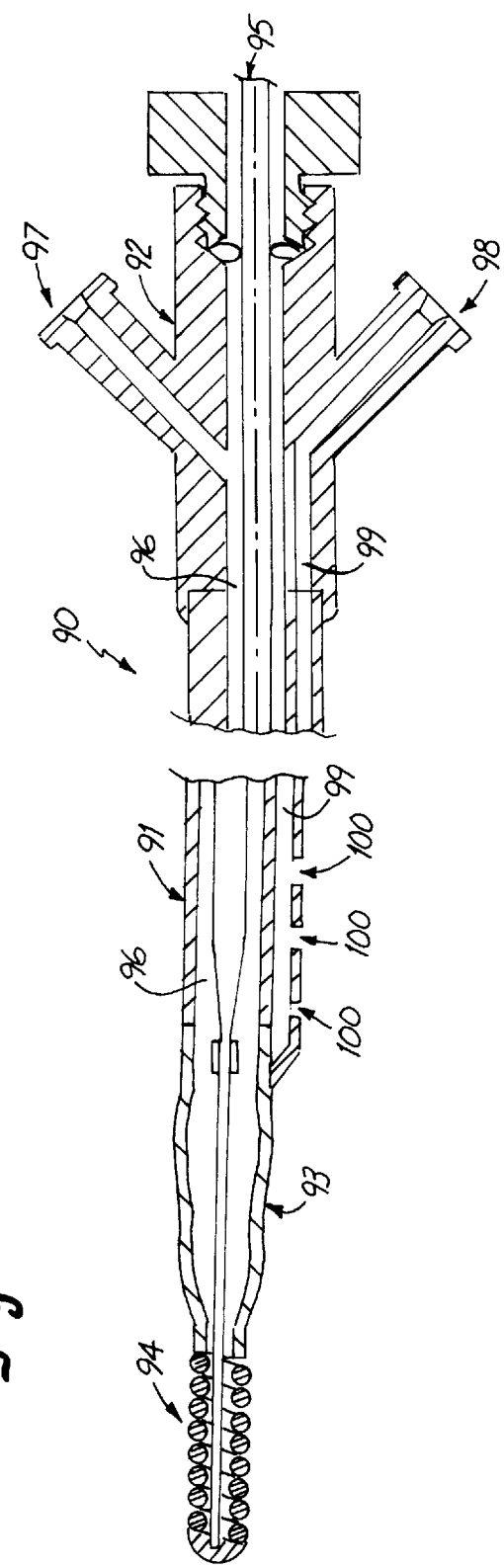

VASCULAR SEALING APPARATUS AND METHOD

This is a Continuation of application Ser. No. 08/549,332 filed Oct. 27, 1995, now U.S. Pat. No. 5,626,601.

BACKGROUND OF THE INVENTION

1. Field of the Invention.

This invention relates, generally, to medical devices. More particularly, the invention relates to hemostatic devices used for arresting the flow of blood or hemorrhage from punctures of the vascular system.

2. Background Information.

Various surgical procedures are performed by medical specialists such as cardiologists and radiologists utilizing percutaneous entry into a blood vessel or body cavity. Examples of such procedures include different techniques to recanalize atherosclerotic blood vessels, such as balloon angioplasty or atherectomy. Recently, both the types and number of procedures performed utilizing the above mentioned percutaneous access to blood vessels have increased greatly.

These procedures generally involve the percutaneous puncture with a thin walled needle into a blood vessel. Following this, a guidewire is placed through the needle into the blood vessel and the needle is withdrawn. An intravascular sheath of variable size is then advanced over the guidewire, percutaneously, into the lumen of the blood vessel. The introducer sheath is then used as an ingress/egress means during the procedure. Following completion of the procedure, the introducer sheath may be removed, but this requires the application of prolonged manual pressure over the puncture site by a physician or other suitably trained medical personnel. The time involved here is frequently extensive since patients are often treated with a variety of anticoagulant and thrombolytic agents, particularly in the setting of a heart attack. Alternatively, the sheath may be left in the puncture site for a prolonged period of time until the patient's coagulation status has returned to normal. Depending on the size of the vascular sheath, there may be an increased risk of bleeding to the patient, which may require blood transfusion. In addition, there is a significant risk for injury to the blood vessel upon removal of the sheath, particularly if the sheath has been in place for a prolonged period of time. This includes the possible development of an pseudo-aneurysm or severe hematoma. The current technique for removal of introducer sheaths is also painful to the patient and requires prolonged bed rest after removal. This adds to the discomfort for the patient, as well as prolonging hospitalization and costs.

Many of the intra-vascular procedures are performed in patients who are clinically unstable or who have the potential to become so, following completion of the procedure. Following removal of the vascular access sheath, it could be cumbersome and sometimes difficult to re-enter the blood vessel if necessary. Thus, with the current technique for removal of the sheath following the procedure, no easy, reliable method is available to allow reaccess to the lumen of the blood vessel, if necessary.

The prior art includes U.S. Pat. No. 4,744,364 to Kensey, U.S. Pat. No. 4,852,568 to Kensey, and U.S. Pat. No. 4,890,612 to Kensey, which disclose a method and device for sealing punctures in blood vessels by injection of a resorbable hemostatic plug into the puncture site. These devices and methods have a number of shortcomings and problems. U.S. Pat. No. 5,383,896 to Gershony et al. discloses a vascular sealing device having a thin conduit with a balloon at a distal end and an elastomeric seal at a proximal end.

Despite the need for a device and method in the art which overcomes the limitations and problems of the prior art, none insofar as is known has been proposed or developed.

SUMMARY OF THE INVENTION

This invention provides a vascular sealing device for effecting closure of a puncture or other opening in a blood vessel, or other body cavity, which has been entered through percutaneous techniques. The device is useable with a standard percutaneous vascular introducer. The vascular sealing device generally comprises a body or shaft, an adapter disposed at a proximal end of the shaft, and a balloon portion disposed generally at a distal end of the shaft. A core wire is connected to the distal end and extends, internally, through a central lumen of the device for deflation of the balloon. A procoagulant is introduced through the introducer, or alternatively through an additional lumen and associated apertures, and to the puncture sealed by the inflated balloon. Subsequently, the balloon is deflated and the device is removed from the sealing puncture, with or without the aid of a reaccess sheath. A method of sealing a puncture site is also disclosed and claimed.

In one embodiment, the medical sealing device body structure adapter has an inflation port communicatively connected to the central lumen. The central lumen is communicatively connected to the inflation member, whereby fluid is introduced in the inflation port and through the central lumen to inflate the inflation member. In this embodiment, the means to introduce a procoagulant is an introducer having an axial lumen opening to a distal insertion end adapted for location in the blood vessel opening, a fluid injection port being communicatively connected to the introducer lumen, the body structure shaft being extended through the introducer lumen so that the inflatable member is disposed outwardly beyond the introducer distal insertion end, procoagulant being introduced to the introducer lumen via the fluid injection port and distributed out the distal insertion end.

In a second embodiment, the medical sealing device body structure adapter has an inflation port and a communicatively connected longitudinal inflation lumen. The inflation lumen is communicatively connected to the inflation member, whereby fluid is introduced in the inflation port and through the inflation lumen to inflate the inflation member. In this embodiment, the means to introduce a procoagulant comprises a procoagulant introduction lumen disposed within the body structure, a procoagulant ingress port disposed on an exterior surface of the body structure and being communicatively connected to the introduction lumen, and at least one procoagulant egress aperture disposed at a predetermined location on the body structure and being communicatively connected to the introduction lumen.

In a third embodiment, the medical sealing device of claim body structure adapter has an inflation port communicatively connected to the central lumen. The central lumen is communicatively connected to the inflation member, whereby fluid is introduced in the inflation port and through the central lumen to inflate the inflation member. In this embodiment, the means to introduce a procoagulant also comprises a procoagulant introduction lumen disposed within the body structure.

Unique aspects of this invention include: (1) the creation of immediate hemostasis at the puncture site for procoagulant delivery; (2) the device balloon acts as a marker for delivery of procoagulant; (3) balloon approach prevents injection of procoagulant into the bloodstream; (4) balloon shape is controllable and blood vessel occlusion is minimized; (5) the balloon has a low profile for placement and removal; and (6) the apparatus and method allow reaccess to the patient's vasculature. Other features, benefits and objects of this invention will become clear from the following description by reference to the drawings.

BRIEF DESCRIPTION OF THE DRAWINGS

FIG. 2 is an axial, crossectional view, broken longitudinally, of the vascular sealing device, in an uninflated state and disposed in an operative orientation through a standard access sheath.

FIG. 3 is a crossectional view of the vascular sealing device shown in FIG. 2, in an inflated state.

FIG. 4 is a crossectional view of the vascular sealing device shown in FIG. 1, in an uninflated state and partially retracted through the vascular access sheath.

FIG. 5 is a view of the vascular sealing device inserted through an introducer sheath and into a patient's vascular system, which is shown enlarged and in section.

FIG. 6 is a view of the vascular sealing device inserted through a vascular introducer or sheath, and being inflated.

FIG. 7 is a view of the vascular sealing device with its balloon portion inflated, and further showing retraction of the vascular introducer.

FIG. 8 is an axial, crossectional view of an alternative embodiment of the vascular sealing device of the present invention.

FIG. 9 is a crossectional view of the vascular sealing device shown in FIG. 8, taken along line 9—9 thereof.

FIG. 10 is a crossectional view of the vascular sealing device taken along line 10—10 of FIG. 8.

FIG. 11 is a crossectional view of the vascular sealing device taken along line 11—11 of FIG. 8.

FIG. 12 is an axial, crossectional view of yet another alternative embodiment of the vascular sealing device of the present invention.

DESCRIPTION OF THE PREFERRED EMBODIMENTS

Figure 1:
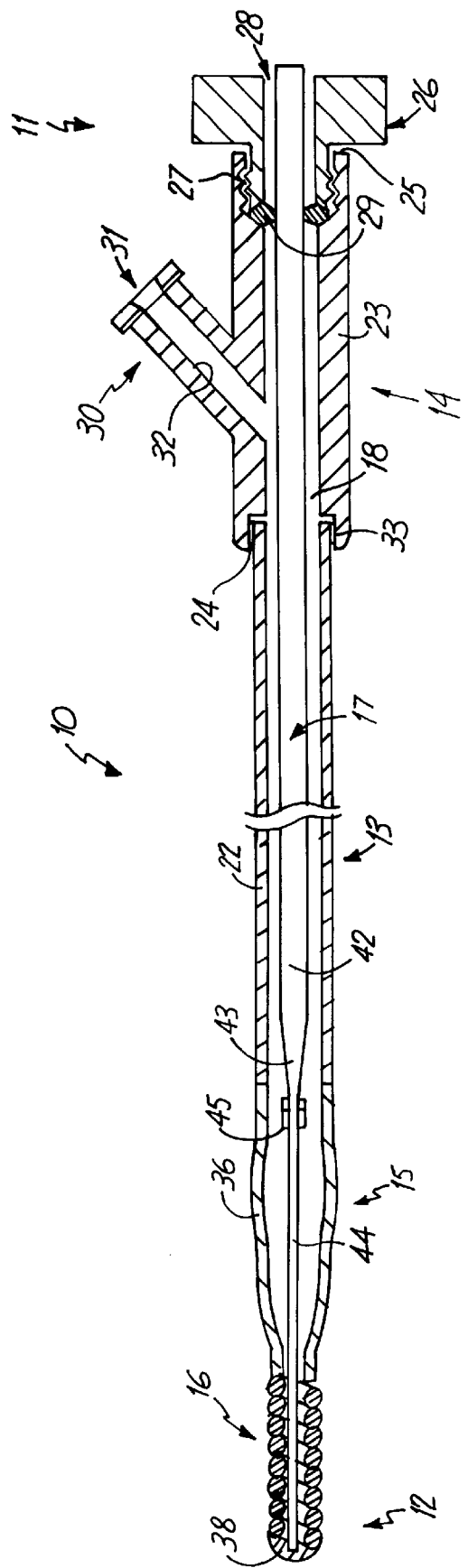
FIG. 1 is an axial, crossectional view, broken longitudinally, of the vascular sealing device of the present invention, in a normal, uninflated state.

FIG. 1 shows a preferred embodiment of the vascular sealing device 10 for effecting closure of a puncture or other opening in a blood vessel which has been entered through percutaneous techniques. The device 10 is useable with a standard percutaneous vascular sheath or introducer. The vascular sealing device 10 has proximal 11 and distal 12 ends. The vascular sealing device 10 generally comprises a body or shaft 13, an adapter or hub 14 disposed at the proximal end of the shaft 13, a balloon 15 portion disposed at the distal end of the shaft 13, and a tip 16 disposed at the distal end of the balloon 15. A core wire 17 is connected to the tip 16 and extends, internally, through a lumen 18 of the device 10. Basically, the proximal end 11 of the device 10 is for manipulation, inflation, and connection to associated medical apparatus described further below, while the distal end 12 is for insertion into the patient's body.

The shaft 13 is rigid and has an elongated cylindrical or tubular configuration. The shaft 13 has a diameter less than the diameter of the access lumen of the introducer or sheath with which it is used, and a predetermined length at least two (2) cm. greater than that of the introducer. Thus, for example for a standard 12 cm. introducer, the shaft 13 would be at least 14 cm. long. A hollow center or lumen 18 extends the entire length of the shaft 13. The proximal end of the shaft 13 is connected to the hub 14 as is described below. The distal end of the shaft 13 is connected to the balloon 15 via heat bonding, an adhesive or other known means. The shaft 13 may be constructed of HDPE, polyimide, nylon, stainless steel, or a combination of such materials, for example.

The hub 14 provides a means of inflating the balloon 15, a means of access to lumen 18, and a means of permitting the movement of core wire 17 while simultaneously preserving the sealed environment of lumen 18. The hub 14 is rigid and has an generally cylindrical configuration. The hub 14 has a body 23 with an integral inflation port arm 30. A hollow center or lumen extends from the proximal end of the hub 14, axially and distally, to communicatively connect with the lumen 18 of the shaft. The inflation port arm 30 is disposed at an angle with respect to the hub body 23 and has a lumen 32 which is communicatively connected to the hub lumen. The arm 30 has an inflation port 31 disposed at its extended end. Preferably, the port 31 has a connector such as a Luer-Lock connector for mating with an inflation device (not shown) as is know in the art. Upon connection of the inflation device to the port 31, the device is actuated by the user to deliver a predetermined amount of fluid into the lumen 18, whereby the balloon 15 is expanded laterally a predetermined distance for vascular sealing purposes. The distal end of the hub 14 has an annular shaft connection bore 33. The shaft 13 is connected in the bore 33 by a suitable connection method. The hub 14 may be constructed of HDPE, polyimide, nylon stainless steel or a combination of such materials for example. The proximal end of the hub 14 has a threaded annular socket 25 for connectably receiving a cap 26. Although the shaft 13 and hub 14 are described herein as being connected, but separate structures, it is specifically within the purview of this invention that they may alternatively form a unitary, integrally formed structure.

The cap 26 has a cylindrical configuration of a predetermined diameter larger than that of the hub 14. A threaded mating end 27 is disposed on the distal end of the cap 26 for connection with the socket 25 of the hub 14. The cap 26 has a proximal access aperture 28 which defines an axial lumen that extends distally and is coextensive with the apparatus lumen 18 when operatively connected. The proximal access aperture 28 permits extension of the core wire 17 therethrough and into the apparatus lumen 18. When connected to the hub 14 and moved distally, the cap 26 connection end 25 engages an O-Ring 29 which is seated in the cap connection end 25 of the hub 14. Cap 26 engagement of the O-Ring 29 creates a seal in the lumen 18 around the core wire 17. Also, in the actuated state, the O-Ring 29 grips the core wire 17 and maintains it in a predetermined longitudinal position.

The balloon 15 is disposed near the distal end of the shaft 13. The balloon 15 body 36 is preferably a tubular structure in an uninflated state with a predetermined slightly tapered (distally) configuration. The balloon body 36 is connected to the shaft body 22 at its proximal end by heat bonding, adhesives or other known means. In an inflated state, the balloon 15 assumes a rounded configuration, preferably elliptical, with a minimum inflated diameter of greater than or equal to two times the french size of the puncture hole 57 being sealed. The height or thickness of the inflated balloon 15 is preferably less than one half the diameter of a typical blood vessel being sealed, so as to minimize obstruction of flow through the blood vessel. The balloon 15 body 36 is preferably constructed of an expandable material such as PE, PET, nylon, natural latex and the like.

The core wire 17 is rigid, elongated and disposed longitudinally in the lumen 18. The majority of the wire 17 has a predetermined, preferably uniform diameter of approximately 0.016 inches. Importantly, the wire 17 is tapered at a predetermined distal region. The proximal end of the wire 17 extends out of the proximal access aperture 28 of the cap 26, a predetermined distance. The core wire 17 is preferably constructed of stainless steel or nickel titanium alloys. Referring, to FIGS. 3 and 4, during an inflation state, retraction of the core wire 17 constricts or compresses the balloon 15 causing it to expand laterally and shrink longitudinally to assume a flat, thin profile with a high sealing diameter. A marker band 45 of platinum or a similar radiopaque material is preferably connected at a predetermined position on the core wire 17 for position indication to the user. Alternatively, the marker band may be connected to the shaft 13. During a deflation state, the core wire 17 is extended distally by the user to longitudinally stretch the balloon 15 to its normal state and thereby shrink the lateral diameter of the balloon 15. This enables the uninflated balloon 15 to assume a low diameter or profile for apparatus 10 removal to minimize trauma to the blood vessel 56 and puncture site 57.

The flexible atraumatic tip or extension 16 is shown disposed at the distal end 12 of the vascular sealing device 10. The extension 16 preferably has a tubular structure with a diameter less than that of the uninflated balloon 15 and shaft 13. The extension 16 is formed of a flexible material, preferably coiled platinum wire. The tip 16 decreases the level of trauma to the vessel wall during insertion and manipulation of the device 10. The tip 16 is preferably slightly angled. The tip 16 has a rounded, solid end portion 38 to which is connected the core wire 17.

Referring to FIGS. 2–7, in use, the vascular sealing device 10 is pre-inserted into the input end 45 of a reaccess sheath 49 as shown in FIG. 2. The reaccess sheath 49 comprises an elongated shaft 52 with a tapered distal end 51 and an ingress/egress hub 50. The reaccess sheath 49 is preferably constructed of Teflon or a similarly lubricious material and fits tightly over the device 10.

As is shown in FIG. 5, the assembly of the uninflated vascular sealing device 10 and the reaccess sheath 49 is first inserted into a standard introducer of vascular sheath 61, which is of a known design and which has been previously positioned through a puncture 57 in the skin surface 58, tissue 59, vessel wall 60 and within a blood vessel 56 of a patient for performance of a medical intravascular procedure. Referring to FIG. 6, the assembly is advanced by manual manipulation until the distal end 12 extends just beyond the distal end of the introducer 61 and into the blood vessel 56. Fluid is then injected, via a known inflating means (not shown), into the device 10 through the inflation port 31 until a predetermined amount of balloon 15 inflation is attained as for example is shown in FIGS. 3 and 6. Next, the device 10 is manually pulled slightly proximally back through the reaccess sheath 49 so that the balloon 15 abuts the distal end 51 of the sheath 49. The core wire 17 is also manually proximally pulled to flatten the profile of the device 10 and minimize disturbance of blood flow in vessel 56. Referring to FIG. 7, the balloon 15 is manually proximally manipulated to effect a hemostatic seal at the blood vessel puncture site 57. Next, and importantly, a procoagulant is injected through a fluid access port 53 of the sheath 61 and is released out its distal end 51 at the puncture site 57. The balloon section 15 remains abutted against the inner vessel wall 56 at the puncture site 57 while the introducer 61 may be retracted. After a predetermined time period, on the order of 1–3 minutes, the balloon 15 is deflated and the core wire 17 is advanced distally to decrease its profile for removal. The reaccess sheath 49 is advanced distally over the deflated balloon 15, as is shown in FIG. 4, and the combined device-sheath assembly may be pulled proximally out of the puncture site 57 along with the introducer 61. Alternatively, the vascular sealing apparatus 10 may be removed proximally away from the reaccess sheath 49, along with the introducer 61, leaving the sheath 49 in place for reaccess with a guide wire, for example. In the later case, the sheath 49 may be removed at a later time, with or without a guidewire remaining in place.

The procoagulant may include one of the following substances or combinations of substances: (1) thrombin, (2) collagen, (3) fibrin/fibrinogen, (4) cyanoacrylate, (5) thrombin and collagen, (6) fibrin/fibrinogen and collagen, (7) cyanoacrylate and collagen, and (8) thrombin and fibrin/fibrinogen.

The advantages of the device 10 and method of the present invention include, but are not limited to, both individually and cooperatively, (1) that the inflated balloon 15 blocks egress of blood immediately upon being properly positioned in the blood vessel at the puncture site to provide fast hemostasis; (2) that the inflated balloon 15 acts as an internal marker to permit the user to accurately gauge the depth of the puncture and the thickness of the tissues surrounding the puncture; and (3) that the inflated balloon 15 acts as a backstop at the inner wall of the blood vessel to (i) precisely position the sealing clot in the puncture and (ii) to prevent procoagulant from entering the patient's circulatory system.

Referring to FIGS. 8–11, an alternative embodiment of the vascular sealing device 66 is shown. The vascular sealing device 66 has proximal 67 and distal 68 ends. The vascular sealing device 66 generally comprises a body or shaft 69, an adapter or hub 70 disposed at the proximal end of the shaft 69, a balloon 71 portion disposed at the distal end of the shaft 69, and a tip 72 disposed at the distal end of the balloon 71. A core wire 73 is connected to the tip 72 and extends, internally, through a lumen 74 of the device 66 and out the proximal end 67.

The shaft 69 is rigid and has an elongated cylindrical or tubular configuration. The shaft 69 has a diameter, preferably uniform, less than the diameter of the access lumen of the introducer or sheath with which it is used, and a predetermined length. The lumen 74 extends the entire length of the shaft 69. The proximal end of the shaft 69 is connected to the hub 70. The distal end of the shaft 69 is connected to the balloon 71. The shaft 69, as well as the other components of this device 66 embodiment, is constructed of materials similar to those of device 10.

The hub 70 is rigid and has an generally cylindrical configuration. The proximal end of the shaft 69 is connected to the distal end of the hub. The proximal end of the hub 70 has a threaded annular socket for connectably receiving a cap 75. A hollow center or lumen extends from the proximal end of the hub 70, axially and distally, to communicatively connect with the lumen 74 of the shaft 69.

The hub 70 has an integral inflation port 77. The inflation port 77 has an interior, hemispherical inflation lumen 78 which extends into the shaft 69 and the balloon 71. The inflation lumen 78 is formed between the outer shaft wall 86 or layer and an inner shaft wall 87. The inner shaft 87 wall further surrounds and defines a portion of the access lumen 74. At the near distal end of the shaft 69, the inner wall 87 merges with the outer wall 86 to form a transition wall 89 at a predetermined distal hemispherical area. The inflation lumen 78 is completely independent of the access lumen 74. Upon connection of the inflation device to the port 77, the device is actuated by the user to deliver a predetermined amount of fluid into the lumen 78 and to the balloon 71, whereby the balloon 71 is expanded laterally a predetermined distance for vascular sealing purposes.

The hub 70 further has a integral injectate or introduction port 79. The injectate port 79 has an interior, hemispherical injectate lumen 80 which extends into the shaft 69 to a plurality of injectate egress apertures 81. The injectate lumen 80 is formed between the outer shaft wall 86 or layer and an inner shaft wall 87. The injectate lumen 80 is completely independent of the access lumen 74 and from the inflation lumen 78. The injectate apertures 81 are disposed in the outer wall 86, a predetermined distance from each other and from the balloon 71. A procoagulant is injected through the injectate port 79, into the injectate lumen 80, and is released at the puncture site 57 through the injectate apertures 81.

The cap 75 has a cylindrical configuration of a predetermined diameter larger than that of the hub 70. A threaded mating end of the cap 75 connects with the hub 70. The cap 75 has a proximal access aperture which permits extension of the core wire 73 therethrough and into the apparatus central access lumen 74. When connected to the hub 70 and moved distally, the cap 75 connection end engages an O-Ring 76 which is seated in the cap connection end of the hub 70. Cap 75 engagement of the O-Ring 76 creates a seal in the lumen 74 around the core wire 73. Also, in the actuated state, the O-Ring 76 grips the core wire 73 and maintains it in a predetermined longitudinal position.

The balloon 71 is disposed near the distal end of the shaft 69. The balloon 71 body 88 is connected to the shaft outer wall 86 and to the transition wall 89, at its proximal end. The body 88 surrounds the distal end of the inner wall 87 to define the balloon 71, which is communicatively connected to the inflation lumen 78.

The core wire 73 is rigid, elongated, disposed longitudinally in the access lumen 74, and has a predetermined length. The majority of the wire 73 has a predetermined diameter with a tapered distal region. The proximal end of the wire 73 extends out of the proximal access aperture of the cap 75, a predetermined distance. The distal end of the wire 73 is connected to the tip 72. A radiopaque marker band 82 is connected at a predetermined position on the core wire 73 for position indication to the user. During a deflation state, the core wire 73 is extended distally by the user to longitudinally stretch the balloon 71 to its normal state and thereby shrink the lateral diameter of the balloon 71.

The flexible atraumatic tip or extension 72 is shown disposed at the distal end 68 of the vascular sealing device 66. The extension 72 preferably has a tubular structure with a diameter less than or equal to that of the uninflated balloon 71 and shaft 69.

FIG. 12, shows another alternative embodiment of the vascular sealing device 90. The vascular sealing device 90 generally comprises a body or shaft 91, a hub or adapter 92 disposed at the proximal end of the shaft 91, a balloon 93 portion disposed at the distal end of the shaft 91, and a tip 94 disposed at the distal end of the balloon 93. A core wire 95 is connected to the tip 94 and extends, internally, through a lumen 96 of the device 90. In this embodiment, balloon inflation fluid is injected in an adapter port 97 which is communicatively connected to the central lumen 96 and to the balloon 93 interior. Also in this embodiment, procoagulant is injected in adapter port 98 which is communicatively connected to an interior lumen 99 which has injectate apertures 100 disposed at predetermined positions proximally adjacent the balloon 93 on shaft 91.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

The invention claimed is:

1. A method for closing a puncture or other opening in a blood vessel, comprising the steps of:
    (a) inserting a balloon apparatus through an introducer which is disposed in the blood vessel opening;
    (b) inflating said balloon apparatus;
    (c) moving said balloon apparatus into contact with the opening sufficient to effect a hemostatic seal at the puncture site;
    (d) introducing a procoagulant to the opening;
    (e) deflating said balloon apparatus; and
    (f) removing said balloon apparatus through the opening and through the procoagulant.

2. The method of claim 1, in which the procoagulant is injected, the introducer is retracted, and balloon deflation is commenced within a time period of about one minute.

3. The method of claim 1, in which the procoagulant is injected, the introducer is retracted, and balloon deflation is commenced within a time period of between about one to three minutes.

4. The method of claim 1, in which the retraction of the introducer is facilitated by the injection of the procoagulant.

5. The method of claim 1, further comprising the step of moving said balloon apparatus into contact with the opening so that the balloon apparatus functions as an internal marker to permit the user to accurately gauge the depth of the puncture and the thickness of the tissues surrounding the puncture.

6. The method of claim 1, in which the step of inserting a balloon apparatus through an introducer which is displaced in the blood vessel opening comprises the step of connecting an elongated and tapered wire member to an inflatable balloon apparatus and configuring the taper of the wire member so that a predetermined distal region has a smaller diameter than a proximal region, and the step of removing said balloon apparatus through the opening comprises removal of the deflated balloon apparatus having the smaller diameter distal region therein so as to reduce the size of the apparatus being withdrawn through the procoagulant clot being formed at the puncture site.

7. The method of claim 1, in which the procoagulant is characterized by its viscous-like properties.

8. The method of claim 7, in which the procoagulant is selected from the group consisting of a liquid and a gel.

9. The method of claim 7, in which the procoagulant is injected through the introducer.

10. The method of claim 7, in which the procoagulant is injected through the balloon apparatus.

11. The method of claim 1, in which the procoagulant fills a portion of the entire depth of the puncture.

12. A method for rapid closure of a puncture or other opening in a blood vessel, comprising the steps of:
   (a) inserting a balloon apparatus through an introducer which is displaced in the blood vessel opening;
   (b) inflating said balloon apparatus;
   (c) moving said balloon apparatus into contact with the opening sufficient to effect a hemostatic seal at the puncture site;
   (d) introducing a procoagulant to the opening by injection through the introducer as the introducer is retracted, and then commencing deflation of said balloon apparatus so that the procoagulant is injected, the introducer is retracted, and the balloon deflation is commenced within a time period of between about one and three minutes;
   (e) deflating said balloon apparatus; and
   (f) removing said balloon apparatus through the opening.

13. The method of claim 12, in which the retraction of the introducer is facilitated by the injection of the procoagulant.

14. The method of claim 12, further comprising the step of moving said balloon apparatus into contact with the opening so that the balloon apparatus functions as an internal marker to permit the user to accurately gauge the depth of the puncture and the thickness of the tissues surrounding the puncture.

15. The method of claim 12, in which the step of inserting a balloon apparatus through an introducer which is displaced in the blood vessel opening comprises the step of connecting an elongated and tapered wire member to an inflatable balloon apparatus and configuring the taper of the wire member so that a predetermined distal region has a smaller diameter than a proximal region, and the step of removing said balloon apparatus through the opening comprises removal of the deflated balloon apparatus having the smaller diameter distal region therein so as to reduce the size of the apparatus being withdrawn through the procoagulant clot being formed at the puncture site.

16. The method of claim 12, in which the procoagulant is characterized by its viscous-like properties.

17. The method of claim 16, in which the procoagulant is selected from the group consisting of a liquid and a gel.

18. The method of claim 16, in which the procoagulant is injected through the balloon apparatus.

19. The method of claim 12, in which the procoagulant fills a portion of the entire depth of the puncture.

20. A method for closing a puncture or other opening in a blood vessel, comprising the steps of:
   (a) inserting a balloon apparatus through an introducer which is disposed in the blood vessel opening;
   (b) inflating said balloon apparatus;
   (c) moving said balloon apparatus into contact with the opening sufficient to effect a hemostatic seal at the puncture site;
   (d) introducing a procoagulant to the opening;
   (e) deflating said balloon apparatus; and
   (f) removing said balloon apparatus through the opening and the procoagulant clot being formed at said opening.

21. The method of claim 20, in which the procoagulant is injected, the introducer is retracted, and balloon deflation is commenced within a time period of about one minute.

22. The method of claim 20, in which the procoagulant is injected, the introducer is retracted, and balloon deflation is commenced within a time period of between about one to three minutes.

23. The method of claim 20, in which the retraction of the introducer is facilitated by the injection of the procoagulant.

24. The method of claim 20, further comprising the step of moving said balloon apparatus into contact with the opening so that the balloon apparatus functions as an internal marker to permit the user to accurately gauge the depth of the puncture and the thickness of the tissues surrounding the puncture.

25. The method of claim 20, in which the step of inserting a balloon apparatus through an introducer which is displaced in the blood vessel opening comprises the step of connecting an elongated and tapered wire member to an inflatable balloon apparatus and configuring the taper of the wire member so that a predetermined distal region has a smaller diameter than a proximal region, and the step of removing said balloon apparatus through the opening comprises removal of the deflated balloon apparatus having the smaller diameter distal region therein so as to reduce the size of the apparatus being withdrawn through the procoagulant clot being formed at the puncture site.

26. The method of claim 20, in which the procoagulant is characterized by its viscous-like properties.

27. The method of claim 26, in which the procoagulant is selected from the group consisting of a liquid and a gel.

28. The method of claim 26, in which the procoagulant is injected through the introducer.

29. The method of claim 26, in which the procoagulant is injected through the balloon apparatus.

30. The method of claim 20, in which the procoagulant fills a portion of the entire depth of the puncture.

31. A method for closing a puncture or other opening in a blood vessel, comprising the steps of:
   (a) inserting a balloon apparatus through an introducer which is disposed in the blood vessel opening;
   (b) inflating said balloon apparatus;
   (c) moving said balloon apparatus into contact with the opening sufficient to effect a hemostatic seal at the puncture site;
   (d) introducing a procoagulant to the opening;
   (e) deflating said balloon apparatus; and
   (f) removing said balloon apparatus through the opening and the procoagulant clot being formed at said opening, with said procoagulant clot substantially simultaneously filling the void resulting from removal of said balloon apparatus.

32. The method of claim 31, in which the procoagulant is injected, the introducer is retracted, and balloon deflation is commenced within a time period of about one minute.

33. The method of claim 31, in which the procoagulant is injected, the introducer is retracted, and balloon deflation is commenced within a time period of between about one to three minutes.

34. The method of claim 31, in which the retraction of the introducer is facilitated by the injection of the procoagulant.

35. The method of claim 31, further comprising the step of moving said balloon apparatus into contact with the opening so that the balloon apparatus functions as an internal marker to permit the user to accurately gauge the depth of the puncture and the thickness of the tissues surrounding the puncture.

36. The method of claim 31, in which the step of inserting a balloon apparatus through an introducer which is displaced in the blood vessel opening comprises the step of connecting an elongated and tapered wire member to an inflatable balloon apparatus and configuring the taper of the wire member so that a predetermined distal region has a smaller diameter than a proximal region, and the step of removing said balloon apparatus through the opening comprises removal of the deflated balloon apparatus having the smaller diameter distal region therein so as to reduce the size of the apparatus being withdrawn through the procoagulant clot being formed at the puncture site.

37. The method of claim 31, in which the procoagulant is characterized by its viscous-like properties.

38. The method of claim 37, in which the procoagulant is selected from the group consisting of a liquid and a gel.

39. The method of claim 37, in which the procoagulant is injected through the introducer.

40. The method of claim 37, in which the procoagulant is injected through the balloon apparatus.

41. The method of claim 31, in which the procoagulant fills a portion of the entire depth of the puncture.

* * * * *